United States Patent
Zhao et al.

(10) Patent No.: US 9,857,377 B2
(45) Date of Patent: Jan. 2, 2018

(54) METHOD FOR QUANTIFICATION OF PROTEOME

(75) Inventors: Haiyi Zhao, Shenzhen (CN); Dahai Jiang, Shenzhen (CN); Bo Wen, Shenzhen (CN); Jian Wang, Shenzhen (CN); Jun Wang, Shenzhen (CN); Huanming Yang, Shenzhen (CN); Jin Zi, Shenzhen (CN); Yan Ren, Shenzhen (CN); Siqi Liu, Shenzhen (CN)

(73) Assignee: BGI TECH SOLUTIONS CO., LTD., Shenzhen (CN)

( * ) Notice: Subject to any disclaimer, the term of this patent is extended or adjusted under 35 U.S.C. 154(b) by 733 days.

(21) Appl. No.: 14/369,825

(22) PCT Filed: Dec. 31, 2011

(86) PCT No.: PCT/CN2011/002241
§ 371 (c)(1),
(2), (4) Date: Aug. 29, 2014

(87) PCT Pub. No.: WO2013/097059
PCT Pub. Date: Jul. 4, 2013

(65) Prior Publication Data
US 2015/0141290 A1    May 21, 2015

(51) Int. Cl.
*G01N 33/68* (2006.01)
*G06F 19/18* (2011.01)
*H01J 49/00* (2006.01)

(52) U.S. Cl.
CPC ......... *G01N 33/6848* (2013.01); *G01N 33/68* (2013.01); *G06F 19/18* (2013.01); *H01J 49/0036* (2013.01); *G01N 2570/00* (2013.01)

(58) Field of Classification Search
None
See application file for complete search history.

(56) References Cited

U.S. PATENT DOCUMENTS

2011/0039287 A1    2/2011  Morita et al.

FOREIGN PATENT DOCUMENTS

CN    102128882 A    7/2011
WO    2008/081849 A1    7/2008

OTHER PUBLICATIONS

Grossmann et al. (2010) "Implementation and evaluation of relative and absolute quantification in shotgun proteomics with label-free methods," J. Proteomics. 1740-1746.
Organ et al. (2011) "Quantitative Phospho-Proteomic Profiling of Hepatocyte Growth Factor (HGF)-MET Signaling in Colorectal Cancer," J. Proteome Res. 10(7):3200-3211.
Wang et al. (2010) "The application of label-free quantitative method in mouse spermatogenesis related proteome," Acta Universitatis Medicinalis Nanjing. 30(12):1677-1682.—English abstract provided only, 2 pgs.
Wang et al. (2010) "An Informatics-assisted Label-free Quantitation Strategy that Depicts Phosphoproteomic Profiles in Lung Cancer Cell Invasion," J. Proteome Res. 9(11):5582-5597.
Zhang et al. (2011) "Development of Algorithms for Mass Spectrometry-based Label-free Quantitative Proteomics," Progress in Biochemistry and Biophysics. 38(6):506-518.—English abstract only.
International Search Report with Written Opinion corresponding to International Patent Application No. PCT/CN2011/002241, dated Oct. 18, 2012, 9 pgs.

*Primary Examiner* — Christopher M Gross
(74) *Attorney, Agent, or Firm* — Lathrop Gage LLP (57) ABSTRACT

The present invention relates to a method for quantifying the relative content of a protein in a sample. The present invention also relates to a method for comprising the relative content of a protein in at least two samples.

13 Claims, 4 Drawing Sheets

METHOD FOR QUANTIFICATION OF PROTEOME

RELATED APPLICATIONS

This application is a U.S. National phase of PCT/CN2011/002241 filed Dec. 31, 2011, which is incorporated herein by references.

TECHNICAL FIELD

Embodiments of the present disclosure generally relate to a field of mass spectrometric analysis, more particularly, to analysis of label free quantification with proteome.

BACKGROUND

With gradual development of mass spectrum application in proteomics field, proteomic quantification, particular proteomic label free quantification, has been rapidly developed. The basic principle of label free quantification is to use data obtained by liquid chromatogram-mass spectrum technology for representing expression amount of peptide/protein in a sample. Such method mainly comprises two types:

One is performing quantification by directly using LC-MS/MS (also known as spectra counting). Since this type of quantification method has a relative higher requirement to resolution and sensitivity of mass spectrum, it has not been widely used as current mass spectrum is not able to accurately represent quantification information of peptide/protein.

The other one is performing quantification by using primary mass spectrogram of LC-MS (also known as counting). Such method quantifies a peptide (protein) based on area under curve (or intensity) of extracted ion chromatogram (XIC) which is constructed with primary mass spectrogram. As same or similar peptides (peak of isotope) which are initially separated using liquid chromatography after being digested, present in regions having similar retention times. The high concentration of peptide in the sample, the stronger response intensity of ion signal thereof, thus the result obtained by such method is relative accurate.

Said the other method may be performed by two ways: quantification without identification result (or known as quantification prior to identification) and quantification with identification result (or known as identification prior to quantification).

The quantification without identification result directly subjects information of primary mass spectrogram of LC-MS to peptide quantification and identification, which mainly comprises following steps of: 1) signal preprocessing and peak detection; 2) constructing XIC; 3) aligning retention times; 4) data normalization; 5) sequence matching of peptide/protein; 6) calculating a ratio of protein abundance value; and 7) statistical analysis. Such method is able to quantify more peptides and proteins, however, the quantified peptides have a high false positive error and a large interference of noise peak.

Since the last year, people prefer using quantification with identification result. The basic principle of such method is identifying peptide (protein) firstly by secondary mass spectrogram (LC-MS/MS), then aligning the identified peptide (protein) to corresponding ion peak in primary mass spectrogram (LC-MS), and then constructing a corresponding XIC for label free quantification. Thus, such method not only reduces the false positive error, but also improves accuracy of quantification, as well as decreases time-consumption. Said method comprises general steps of: 1) searching secondary mass spectrogram based on database, to identify peptide (protein) which are subjected to quality control; 2) for the identified peptide (protein), constructing corresponding XIC with primary mass spectrogram thereof; 3) calculating a ratio of abundance values of same protein in different samples; 4) subjecting the calculated result to statistical analysis. Although less peptides (protein) can be quantified using said method, the identified peptides (protein) is obtained by identifying directly using identification software, those ions of peptides in primary mass spectrogram which cannot be identified by the secondary mass spectrogram are not subjected to identification. Therefore, the quantified peptides (proteins) obtained by said method have a high accuracy, which greatly reduce time-consumption for analysis.

As advantages of the quantification with identification result itself, many software have already used said method so far, for example IDEAL-Q, pview, etc. These software all have advantages and disadvantages respectively.

For example, advantage of IDEAL-Q lies in using identification result for cross prediction, which significantly improve quantification coverage. However, triple validation method (isotope peak patter, charge status, signal to noise ratio), used by IDEAL-Q in quality control, is proper, because for the most advanced mass spectrometry LTQ-Orbtrap, which has a high accuracy, is no longer suitable to filter through signal to noise ratio, otherwise many real-existing ions of peptides in the primary mass spectrometry with relative lower signal intensity will be filtered out, which cannot reflect real-existing status of a certain peptide in sample. Besides, the method of calculating area under curve with the constructed XIC by IDEAL-Q is not accurate enough.

As another example, advantage of pview mainly lies in being able to simultaneously handle hundreds of samples; however it requires a large memory (at least 4G) without cross prediction and verification step.

In proteomic quantification, the method of quantifying peptides (proteins) with mass spectrometry usually comprises two steps of: calculating abundance value of peptide firstly, then calculating abundance value of protein.

The step of calculating abundance value of protein mainly uses a relationship between signal intensity of peptides in the primary mass spectrometry and abundance value of peptides, i.e., obtaining the abundance value of peptides by signal intensity of mass spectrometry.

The step of calculating abundance value of protein is to obtain abundance value (or ratio of abundance values) of proteins. The method of aligning the abundance value of peptide to abundance value of protein; will directly be related to accuracy of the step of calculating abundance value of protein.

Currently, commonly-used algorithm for aligning the abundance value of peptide to the abundance value of protein comprises: 1) for each protein, calculating a mean value of abundance values of all peptides in the protein, i.e., the abundance value of the protein, then calculating a ratio of abundance values of the protein between samples using the calculated abundance value of the protein; 2) for each protein, calculating a mean value of the first n peptides (n is an integer being more than 1, for example the first 3) having the maximal abundance values in the protein of the sample, i.e. the abundance value of the protein, then calculating a ratio of abundance value of the protein in samples using the calculated abundance value of the protein; 3) for each protein, calculating a ratio of abundance values of all peptides in the protein of samples firstly, then calculating a mean value or a weighted value of these ratios, being as a ratio of abundance value of the protein of samples.

Mass spectrometry of protein aims at peptides with different properties, even for one same peptide, the mass spectrometry will generate different signals of mass spectrometry under same condition. Thus, even peptides digested from one same protein, which theoretically have same concentrations, the obtained abundance value of mass spectrometry may be much different.

The above two algorithm of 1) and 2) both take a mean value of abundance values of all peptides or the first n of peptides having the maximal abundance values as the abundance value of protein, of which strategy obviously leads to a large derivation. The above algorithm 3) subjects the abundance values of all peptides in the proteins of different samples to alignment, of which disadvantage lies in being unable to providing the abundance value of the protein in single sample; and the disadvantage of the above two algorithm also presents by using all peptides.

Currently, in proteomic quantification (particularly label free quantification), a method which simultaneously improve quantification coverage and/or accuracy is still urgent needed.

SUMMARY

To simultaneously increase quantification coverage and/or accuracy in proteomic quantification (particularly label free quantification), the present disclosure improves the method of verifying identification and prediction of peptides, by which the presence of more peptides may be verified more accurately. The present disclosure uses a new method for calculating a ratio of protein abundance values between samples, i.e., a weighted mean of first 3 peptides having the maximum abundance values included in each of the proteins is taken as abundance value of the proteins, which are used in calculating the ratio of the protein abundance values between samples. Such method may selectively use mass spectrometric data having better quality obviously, which may improve accuracy of the ratio of the protein abundance values, so as to improve accuracy of statistical analysis. It has proved by tests that such method is more accurate than existing method in the prior art.

In a first aspect, there is provided a method of quantifying protein abundance in a sample. According to embodiments of the present disclosure, the method may comprise following steps:

1) obtaining primary mass spectrogram and secondary mass spectrogram from one sample, and predicting peptides corresponding to each of the secondary mass spectrogram;

according to embodiments of the present disclosure, after the step 1), preferably the method may further comprise following steps:

1-1) based on the predicted peptides and charges brought thereof, calculating mass-to-charge values of all isotopes of the predicted peptides and abundance values thereof in nature; and subjecting first n of the isotopes having the maximum abundance values in the mass-to-charge values of the predicted peptides to aligning and matching to all ions in corresponding primary mass spectrogram, wherein n is 2 to 20, preferable 2 to 10, more preferably 2 to 5, most preferably 3, wherein if the corresponding isotope ion corresponded to the abundance value of n can be matched, then such predicted peptide is used in subsequent steps;

2) determining proteins to which the predicted peptides belong, to obtain a protein corresponding to the primary mass spectrogram;

3) for each of the predicted peptides, selecting time intervals located respectively at both sides of a retention time corresponded to the predicted peptides in the primary mass spectrogram, finding spectra peaks having a mass-to-charge value corresponded to an ion of the predicted peptides within the time intervals, wherein the spectra peaks are extracted ion chromatograms of the predicted peptides; wherein the selected time intervals in the step 3) is 130 to 50 second, preferably is 120 to 60 second, most preferably is 90 second; and the selected time intervals located respectively at both sides of a retention time may be same or different;

according to embodiments of the present disclosure, after the step 3), preferably the method may further comprise following steps:

3-1) subjecting the extracted ion chromatograms to a filtration for step 4), comprising:

for overlapping peaks presenting within an interval having a preset retention time, i.e., a plurality of peaks present in the interval having the preset retention time, removing a chromatographic peak having an area under peak smaller than 50% of a total area under peak of all chromatographic peaks presenting in the interval having the preset retention time.

4) calculating area under peak of the extracted ion chromatograms as a quantification indicator of the predicted peptides, wherein an approach of trapezoid area is used for calculating area under peak of the extracted ion chromatograms;

preferably the quantification indicators of all peptides in the sample are subjected to normalization, to obtain a relative quantification indicator of the peptides, for example, the normalization is at least one selected from a group consisting of:

linear regression normalization, quantile normalization, and central tendency normalization, the relative quantification indicator is subjected to step 5) instead of the predicted peptides;

according embodiments of the present disclosure, after the step 4), preferably the method may further comprise following steps:

4-1) in the predicted peptides corresponded to the protein, removing the quantification indicator or the relative quantification indicator which is an obvious outlier;

5) for each of the proteins in the step 2), taking a weighted mean of the quantification indicators as the protein abundance in the sample with first 2 to 20 of the predicted peptides, preferably first 2 to 10 of the predicted peptides, more preferably first 2 to 5 of the predicted peptides, for example first 3 of the predicted peptides having the maximum intensities.

In a second aspect, there is provided a method of comparing a relative abundance of a protein in samples. According to embodiments of the present disclosure, the method may comprise following steps:

1) obtaining primary mass spectrogram and secondary mass spectrogram from two or more of the samples, and predicting peptides corresponding to each of the secondary mass spectrogram;

1-1) based on the predicted peptides and charges brought thereof, calculating mass-to-charge values of all isotopes of the predicted peptides and abundance values thereof in nature; and subjecting first n of the isotopes having the maximum abundance values in the mass-to-charge values of the predicted peptides to aligning and matching to all ions in corresponding primary mass spectrogram, wherein n is 2 to 20, preferable 2 to 10, more preferably 2 to 5, most preferably 3, wherein if the corresponding isotope ion corresponded to the abundance value of n can be matched, then such predicted peptide is used in subsequent steps.

2) determining proteins to which the predicted peptides belong, to obtain a protein corresponding to the primary mass spectrogram;

3) for each of the predicted peptides, selecting time intervals located respectively at both sides of a retention time corresponded to the predicted peptides in the primary mass spectrogram, finding spectra peaks having a mass-to-charge value corresponded to an ion of the predicted peptides within the time intervals, wherein the spectra peaks are extracted ion chromatograms of the predicted peptides; wherein the selected time intervals in the step 3) is 130 to 50 second, preferably is 120 to 60 second, most preferably is 90 second; and the selected time intervals located respectively at both sides of a retention time may be same or different;

according to embodiments of the present disclosure, preferably the method may further comprise following steps:

3-1) subjecting the extracted ion chromatograms to a filtration for the step 4), comprising:

for overlapping peaks presenting within an interval having a preset retention time, i.e., a plurality of peaks present in the interval having the preset retention time, removing a chromatographic peak having an area under peak smaller than 50% of a total area under peak of all chromatographic peaks presenting in the interval having the preset retention time;

4) calculating area under peak of the extracted ion chromatograms as a quantification indicator of the predicted peptides, wherein an approach of trapezoid area is used for calculating area under peak of the extracted ion chromatograms;

5) for each of the samples, subjecting the quantification indicators deriving from all of the predicted peptides to normalization, to obtain a relative quantification indicator of the predicted peptides, for example, the normalization is at least one selected from a group consisting of:

linear regression normalization, quantile normalization, and central tendency normalization.

according to embodiments of the present disclosure, preferably the method may further comprise following steps:

5-1)) for each of the samples, subjecting the quantification indicators deriving from all of the predicted peptides to normalization, to obtain a relative quantification indicator of the predicted peptides;

6) for each of the proteins in step 2), taking a weighted mean of the relative quantification indicator as the relative abundance of the protein in the samples with first 2 to 20 of the predicted peptides in each of the samples, preferably first 2 to 10 of the predicted peptides in each of the samples, more preferably first 2 to 5 of the predicted peptides in each of the samples, for example first 3 of the predicted peptides in each of the samples having the maximum intensities;

7) calculating an abundance ratio of the protein between two of the samples using the relative abundance of the protein, and preferably further comprising:

8) determining whether significance of the protein abundance presents in different samples based on the abundance ratio.

The method of the present disclosure uses a method of verifying identification and prediction of peptides by combing accurate theoretical isotope pattern method (ATIPM) with charge state, which may not only improve quantification coverage, but also improve accuracy of protein quantification. The method of the present disclosure uses cross prediction combing ATIPM for verification, which obviously improved quantification coverage comparing with similar software such as IDEAL-Q, resulting in more quantification with about 30% proteins than IDEAL-Q averagely.

In the method of the present disclosure, a weighted mean of the first m (m is 2 to 20, preferably 2 to 10, more preferably 2 to 5, for example 3) of peptides having maximum abundance values is used for calculating protein abundance value and ratio thereof, which has been subjected to test using a group of standard data. It has find that such the method of the present disclosure is superior to traditional methods (shown in EXAMPLE part below).

DETAILED DESCRIPTION

The method of the present disclosure overcomes disadvantages in prior art, which may be used to realize cross prediction with identification results, and subject the verification (quality control of the verification result) to modification (the above-mentioned ATIPM combining charge state). Besides, on the basis of the method according to embodiments of the present disclosure, it may provide an entire method of statistical analysis for subsequently finding proteins having a significant difference in expression quantity, so as to directly provide information of proteins having a significant difference and related cartogram, which generates an accurate and confident result. To simultaneously improve quantification coverage and/or accuracy, the method of verifying identified and quantified peptides according to embodiments of the present disclosure has been improved, by which presence of more peptides may be verified more accurately. The method according to embodiments of the present disclosure is based on a strategy of performing identification prior to performing quantification.

According to embodiments of the present disclosure, during performing primary mass spectrogram, after separation using liquid chromatography, same or similar peptides (such as isotope ions) are collected and fixed in a liquid chromatography (LC) column; then the collected and fixed peptides are eluted and subjected to mass spectrum in a chronological order, by which ions of same or similar peptides distribute in a certain time quantum. A retention time is a time recording the ions of peptides pass through the mass spectrum, which are eluted from the liquid chromatography column.

Figure 1:
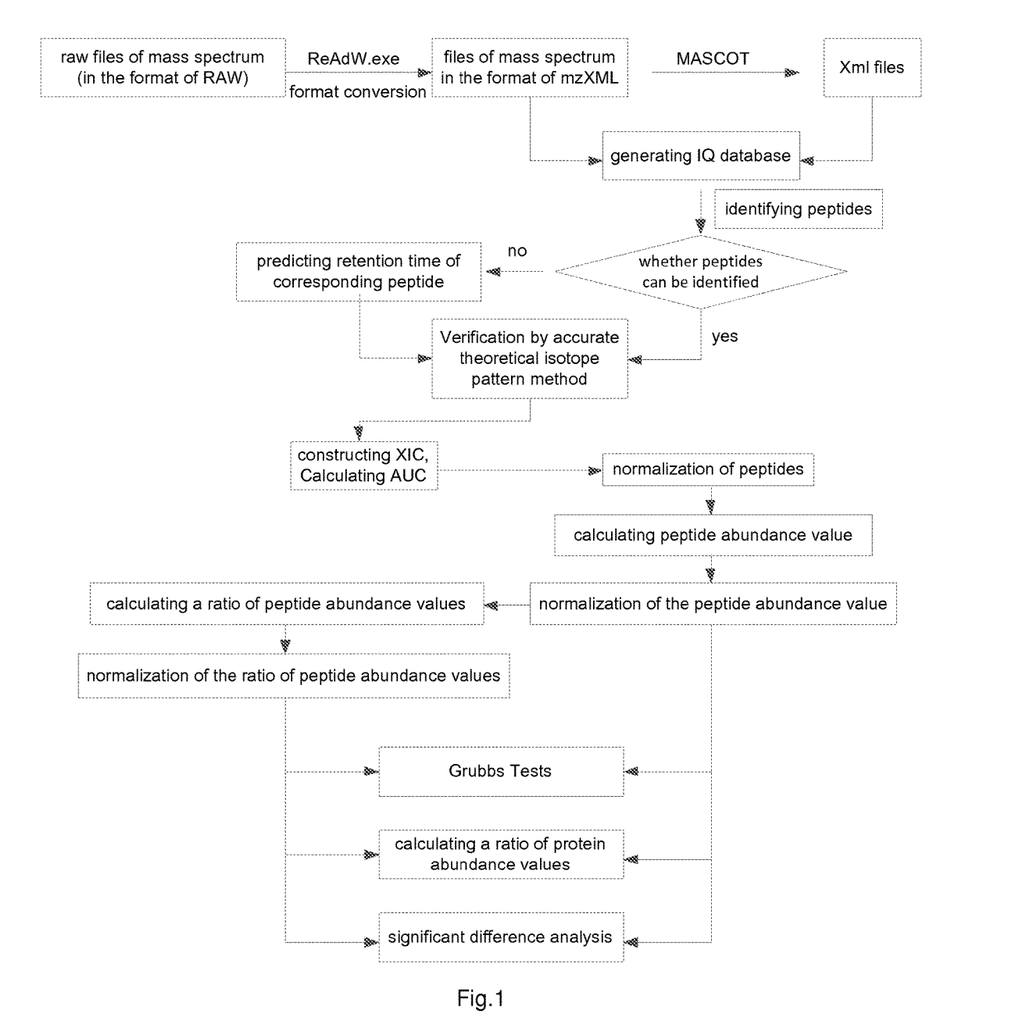
FIG. 1 is flow chart showing a method according to embodiments of the present disclosure.

In some embodiments of the present disclosure, there is provided a proteomic label free quantification method. According to some embodiments, the method comprises following steps (see below and FIG. 1):

1) for one sample to be quantified, obtaining successive primary mass spectrogram and secondary mass spectrogram by LC-MS/MS liquid chromatography mass spectrum; is then identifying theoretical peptides corresponded to the secondary mass spectrogram by searching theoretical database, by which identification of peptides is completed.

2) screening the identified peptides by: based on the identified or the predicted peptides and charges brought thereof, calculating mass-to-charge values of all isotopes of the predicted peptides and abundance values thereof in nature; and subjecting first n (n is 2 to 20, preferable 2 to 10, more preferably 2 to 5, most preferably 3) of the isotopes having the maximum abundance values in the mass-to-charge values of the predicted peptides to aligning and matching to all ions in corresponding primary mass spectrogram, wherein if the corresponding isotope ion corresponded to the abundance value of n can be matched, then such predicted peptide is used in subsequent steps;

3) merging the above predicted or identified peptides into a protein belonged thereof, by which the identification of protein has been completed; then the theoretical peptides corresponded to ions used in performing the second mass spectrum which are selected in performing the primary mass spectrum and proteins belonged thereof are obtained.

4) constructing extracted ion chromatograms (XIC) with real-existing peptides verified in the step 2), and calculating area under curve (AUC). For one peptide, XIC is constructed from corresponded primary mass spectrogram in accordance with following steps: selecting time intervals located respectively at both sides of a retention time corresponded to the predicted peptides in the primary mass spectrogram, finding spectra peaks having a mass-to-charge value corresponded to an ion of the predicted peptides within the time intervals, wherein the spectra peaks are extracted ion chromatograms of the predicted peptides;

5) calculating area under curve of the extracted ion chromatograms as following steps: firstly subjected the constructed XIC to filtering by: for overlapping peaks presenting within an interval having a preset retention time, i.e., a plurality of peaks present in the interval having the preset retention time, removing a chromatographic peak having an area under peak smaller than 50% of a total area under peak of all chromatographic peaks presenting in the interval having the preset retention time; and calculating the reserved AUC of XIC after the step of filtering using an approach of trapezoid area, by which such calculated AUC is taken as a quantification indicator of is peptides;

6) normalization of the quantification indicator of peptides: for each sample (corresponding to each run of LC-MS/MS experiment), all quantification indicators of the peptides are subjected to global normalization, to obtain relative quantification indicator of the peptides;

7) merging peptides into protein and removing outliers: each of the proteins identified in the step 3) comprises a plurality of real-existing peptides verified in the step 2); peptides having the relative quantification indicators which are obvious outliers are preferably removed from the plurality of real-existing peptides, to reduce deviation when calculating protein abundance value in next step;

8) calculating protein abundance value: for each of the proteins, a weighted mean of the first m (m is 2 to 20, preferably 2 to 10, more preferably 2 to 5, for example 3) of peptides having the maximum quantification indicator of the peptides is taken as an abundance value of the proteins in the sample, to obtain a relative content of the protein in the sample (the weighted mean refers to: the weighted mean of each peptide is a proportion of a quantified value of said peptide in the total quantified values of m peptides).

According to some other embodiments, there is provided a proteomic label free quantification method. According to embodiments of the present disclosure, the method mainly directs to comparing a relative abundance value of a protein in two or more samples, which comprises following steps (referring to FIG. 1 below):

1) the abundance values of each protein in each of the samples obtained in the step 1) to 8) is used for calculating a ratio of the abundance values of the proteins in different samples;

2) difference analysis with the ratio of protein abundance values: by means of the ratio of the abundance values, the relative contents of each protein in different samples are compared to determine whether a significant difference exists.

The proteomic label free quantification method of the present disclosure is explanatory illustrated combining with FIG. 1 below.

In an embodiment of the present disclosure, for identifying peptides with mass spectrum data, raw data may be divided into two parts: one part is identification result obtained by commercially identification software mascot with a format of xml, the other part is raw mass spectrum data which is generated from mass spectrum and converted into a format of mzxml, by which data deriving from different experiments may be subjected to cross prediction by a method same as IDEAL-Q.

In an embodiment of the present disclosure, the identified and the predicted peptides are subjected to quality control. The verification method of the present disclosure is mainly based on combining accurate theoretical isotope pattern method (ATIPM) with charge state. Advantage of such verification method is that peptides of the primary mass spectrum are not subjected to signal intensity, which may verify peptides having lower signal intensity. In details, such method comprises: according to the identified or the predicted peptides and charges brought thereof, software package IPC from PNNL (Pacific Northwest NATIONAL LABORATORY) company is provided for calculating all isotope atomic weighs and mass-to-charge values of the peptides and abundance values thereof in nature, and subjecting the first n (n is natural number, preferably is 3) of the isotopes having the maximum mass-to-charge abundance value to aligning and matching to the corresponding peptides in the primary mass spectrum. If the peptides to be verified can be matched within a given range of variations, it indicates that the peptides to be verified is real-existing, all of which may be uses in next step of analysis. Such verification method directly bases on isotope distribution of each element of the theoretical peptide in nature to calculate theoretical distribution of the peptides in nature, which may reflect isotope distribution pattern of the peptide in the sample, so as to verify real-existing peptides having a relative lower mass spectrum signal intensity.

In an embodiment of the present disclosure, the step of constructing the extracted ion chromatogram (XIC) comprises: firstly taking the retention time as X-coordinate, for ion to be construct XIC, selecting a certain range (time interval) of the retention time located at both sides of one retention time corresponded to the ion, finding ions having mass-to-charge similar to the ion of target peptide with the certain range of the retention time, and taking ion intensity as Y-coordinate, by which ion chromatogram peak of the corresponding peptide is obtained.

In an embodiment of the present disclosure, the step of calculating the area under curve (AUC) is shown below: firstly subjecting the constructed XIC to a fitting filtration in accordance with ion intensity, if a peak corresponding to target ion having an area under curve smaller than 50% of a total area under peak of all chromatographic peaks presenting in the give range of the retention time, then such peak is regarded as noise peak which can be directly removed; and then calculating area under curve using an approach of trapezoid area after remove the above-mentioned deviated ion chromatogram peak. Such method may more effectively use information of each available ion in the XIC, which may better indicate a relationship between characteristics of mass spectrum data and real concentration with more accurate result.

In an embodiment of the present disclosure, for the step of subjecting quantification indicator of the peptides to normalization: the main purpose of the data normalization is to eliminate system error of peptide signal among different experiments. In mass spectrum experiment, due to reasons of different ionization efficiencies, spectrum sampling effect, and etc, even different peptides having a same concentration in the same experiment, or same peptides having a same concentration in different experiments, a large deviation may present in signal intensities thereof. Thus, to obtain more accurate quantification result, the step of subjecting the peptide signals to normalization is every necessary. The present disclosure preferably uses following three optional method for normalization: linear regression normalization, quantile normalization, and central tendency normalization.

In an embodiment of the present disclosure, for removing an outlier included in quantification indicators of these peptides in one same protein, Grubbs Test may be used. Prior to calculating the protein abundance value, the ratio of the abundance values, Grubbs Test is firstly used to remove an outlier having a relative smaller value or a relative larger value, by which system error may be further reduces.

In an embodiment of the present disclosure, for calculating the protein abundance value and the ratio of the protein abundance values:

for calculating the protein abundance value, a weighted mean of the first m of peptides having of the maximum peptide abundance values is used;

for calculating the ratio of the protein abundance values: using the first m (m is 2 to 20, preferably 2 to 10, more preferably 2 to 5, for example 3) of peptides having maximum peptide quantification indicators which are quantified to corresponding proteins, and calculating a weighted mean of such m (m is 2 to 20, preferably 2 to 10, more preferably 2 to 5, for example 3) of peptides, in which the weight is a proportion between a value of quantification indicator of each peptide and a total value of quantification indicator of m peptides. It would be appreciated that, theoretically peptides generated by lysing one protein have a same concentration, thus theoretically mass spectrum correspondingly should generate same signal intensity. However, as mass spectrum system error, noise, and influence of mass spectrum to the ionization efficiency resulting from physical and chemical property of the peptide itself present, all of which may result in a relative smaller value of the actual quantification indicator of the peptide, substantially may not result in a relative larger value. Based on such theory, on the one hand, the method of the present disclosure uses the maximum value of the quantification indicator of peptide as much as possible; on the other hand, the method of the present disclosure, balancing requirements of statistical analysis, by which the method according to embodiments of the present disclosure is provided. Through test, it has been found that such method is better than traditional methods indeed (See EXAMPLE 3 below).

In an embodiment of the present disclosure, for difference analysis of the ratio of the protein abundance value: after finishing quantifying all identified peptides, proteins, it may use T-test for subjecting the ratio of the protein abundance values in the sample to significant difference analysis. Two methods of T one-tail test and T two-tail test are used respectively in accordance with data characteristic of peptides, in which the method of T one-tail test directly uses a ratio of same peptides in different samples, a mean thereof is compared with theoretical value, then T test is performed, p-value of each protein is provided. The method of T two-tail test directly uses values of quantification indicators of peptides among samples for comparing, the T test is performed, p-value of each protein is proved. Proteins having significant difference are looked for based on the p-value and the ratio of the protein abundance values.

The method of the present disclosure uses a method of verifying identified and predicted peptides using accurate theoretical isotope pattern method (ATIPM) by combing with charge state, by which not only improves quantification coverage of peptides/protein, but also improves accuracy of protein quantification. The method of the present disclosure uses cross prediction combing ATIPM for verification, which obviously is improved quantification coverage comparing with similar software such as IDEAL-Q, resulting in more quantification with about 30% proteins than IDEAL-Q averagely (See EXAMPLE 1 below). This is because the method of the present disclosure uses accurate theoretical isotope pattern method (ATIPM) for verification, which calculating theoretical distribution of all isotopes of one peptide in nature directly based on intensity of each isotope distribution of every element in the peptide in nature, by which the calculated result of isotope distribution in the peptide in nature is more consistent with real status itself. Thus, peptides present in mass spectrum with a relative lower signal intensity may be verified, which may improve quantification coverage. For calculating area under curve of chromatogram, the method of the present disclosure directly removes an outlier from the constructed chromatograph peaks, i.e., removing those values being obviously inconsistent with normal distribution. Those values being substantially consistent with normal distribution obviously are subjected to cumulative calculating area under curve of the chromatograph peaks using trapezoid area method, by which may more sufficiently use every data in the chromatogram peaks, and the calculated area under curve is more consistent with the result presented by mass spectrum, so as to improve accuracy of the quantification (See EXAMPLE 2 below).

EXAMPLES

Example 1

The present example subjected proteomic whole spectrum secreted by *zymomonas* bacteria to difference analysis. Such analysis comprised two *aeromonas* samples in different culture periods, each sample were triplicate, all of which were subjected to label free quantification analysis using the method of the present disclosure and IDEAL-Q software (obtained from http://ms.iis.sinica.edu.tw/IDEAL-Q/). Specific steps were shown below:

firstly, using mass spectrum raw files in the format of mzxml and mascot identification result in the format of xml as imputing files, setting parameter as default, and subjecting mass spectrum data to quantification analysis using IDEAL-Q; and subjecting the same data to quantification analysis using the method of the present disclosure.

Table 1 was comparison between the number of proteins which could be quantified in two samples. Column of sample 1 and column of sample 2 represented the number of proteins which can be quantified in respective sample alone, column of sample 1 and sample 2 represented the number of proteins which can be quantified in both sample 1 and sample 2. It could be seen from Table 1 that, the quantification coverage obtained by the method of the present disclosure increased 68% on the basis of that of IDEAL-Q in this test, which indicated that the method of the present disclosure may effectively improve quantification coverage.

TABLE 1

Comparison between the number of proteins which could be quantified in two samples

|  | Sample 1 | Sample 2 | Sample 1 and Sample 2 |
| --- | --- | --- | --- |
| the method of the present disclosure | 1756 | 1756 | 1756 |
| IDEAL-Q | 1214 | 1235 | 1043 |
| common | 1127 | 1145 | 963 |

Example 2

Data were duplicate of adult shellfish sample, which were subjected to label free quantification analysis using IDEAL-Q and the method of the present disclosure. Specific steps were shown below:

1) using raw files in the format of mazml and mascot identification result in the format of xml as inputting files, subjecting to quantification analysis using IDEAL-Q; subjecting quantified values of every protein between two samples to linear fitting;

2) subjecting the same data to quantification analysis using the method of the present disclosure; and subjecting distribution of protein quantified value between the samples to linear fitting.

Figure 2:
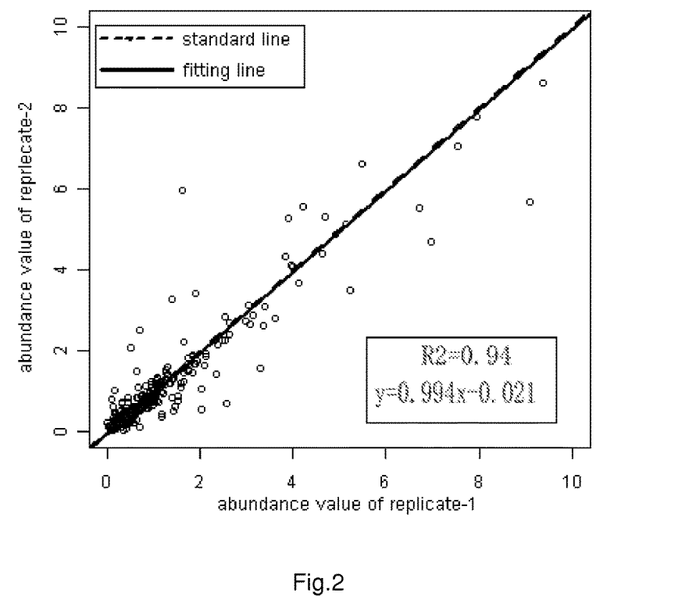
FIG. 2 is a graph showing a ratio regression of protein quantification in two samples according to a method of the present disclosure.
Figure 3:
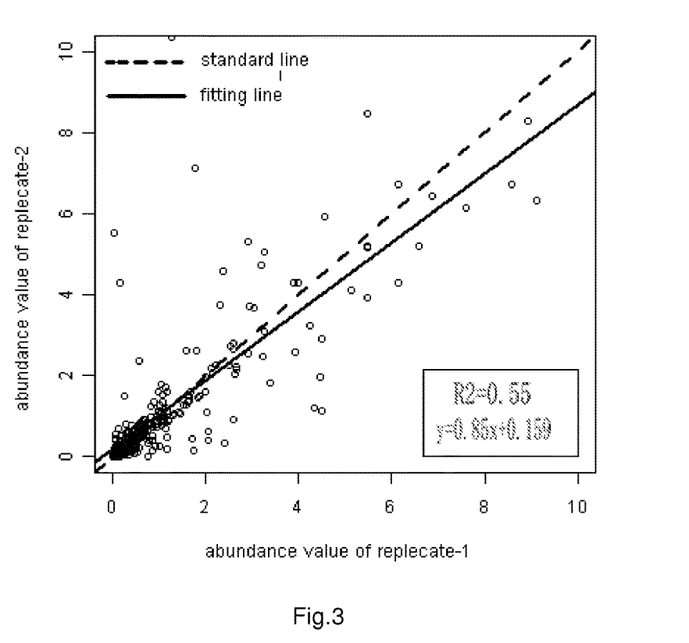
FIG. 3 is a graph showing a ratio regression of protein quantification in two samples using IDEAL-Q.

The obtained results were shown in FIG. 2 and FIG. 3, in which FIG. 2 is a fitting line of abundance ratio of quantified proteins using the method of the present disclosure (fitting with a line y=x, hereinafter), with a correlation coefficient of $R^2=0.94$, and the fitting line (y=0.994x−0.021) substantially overlapped with a standard line, FIG. 3 is a fitting line of abundance ratio of quantified protein using IDEAL-Q, with a correlation coefficient of $R^2=0.55$, and the fitting line (y=0.85x+0.159) is quite different from a standard line. It could be seen from the result that, repeatability of the quantification method according to the method of the present disclosure is much higher than that of IDEAL-Q, i.e., accuracy of the method in the present disclosure is higher than that of IDEAL-Q.

Example 3

The used standard data derived from testing data in an article introducing software T3PQ (http://fgcz-data.uzh.ch/public/T3PQ.tgz). 10 samples were included in such data sets, in which complex yeast lysate having same concentration and same content were used as background material, to which a standard protein fetuin having 10 linear-increased concentrations (0, 20, 40, 60, 80, 100, 120, 160, 200 and 300 fmol/L) were respectively added. To compare with IDEAL-Q method of calculating protein abundance value (a ratio of the protein abundance values), firstly as more peptides included in proteins as possible were quantified with a quantification indicator using IDEAL-Q method; then the protein abundance value and the ratio of protein abundance values were calculated respectively by both existing method in prior art (mainly including calculating protein by means of abundance values of all peptides and a mean value of the first 3 peptides having the maximum abundance values, and calculating a ratio of protein abundance by directly comparing a mean value of peptide ratio, a weighted mean value of peptide ratio or protein abundance value) and the method in the present disclosure. Based on current literature (see to Jonas Grossmann, Bernd Roschitzki1, Christian Panse1, Claudia Fortes, Si mon Barkow-Oestenreicher, Dorothea Rutishauser, Ralph Schlapbach; *JOURNAL OF PROTEIMICS*; 2010; 1740-1746), the existing method of quantifying protein by means of a mean value of the first 3 peptides having the maximum abundance value was better than other methods.

Thus, such method was compared with the method of the present disclosure. Specific steps were shown below: 1) imputing raw mass spectrum files in the format of mzxml and mascot identification result files in the format of xml, setting parameter as default; 2) extracting quantification indicator of peptides included in a standard protein in samples quantified by IDEAL-1; 3) calculating and comparing abundance values of the standard protein in 10 samples obtained by the method of the present disclosure and the mean method using the first 3 peptides having the maximum abundance value, all of which were compared with a theoretical value.

Figure 4:
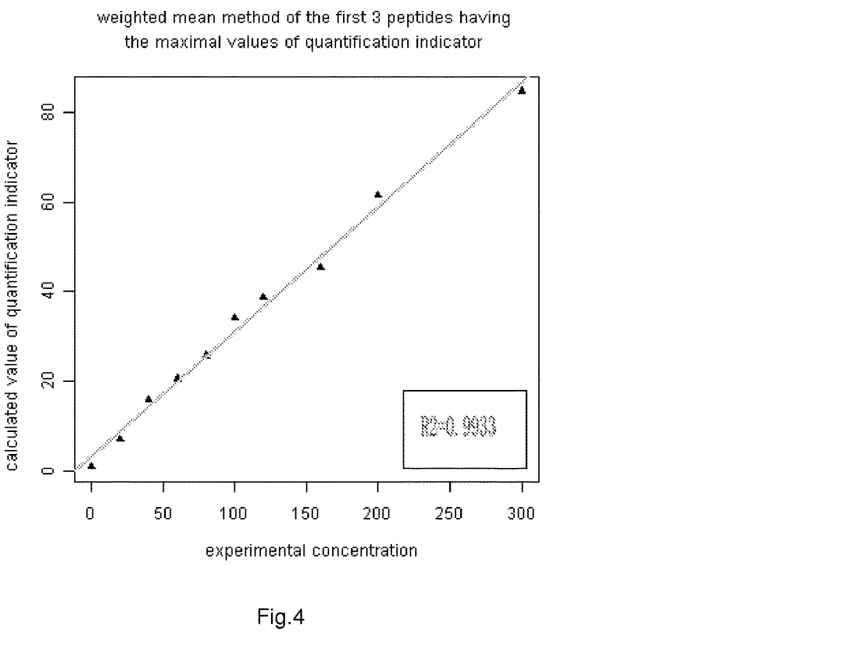
FIG. 4 is a distribution graph showing protein abundance value using a weighted mean of first 3 peptides according to embodiments of the present disclosure.
Figure 5:
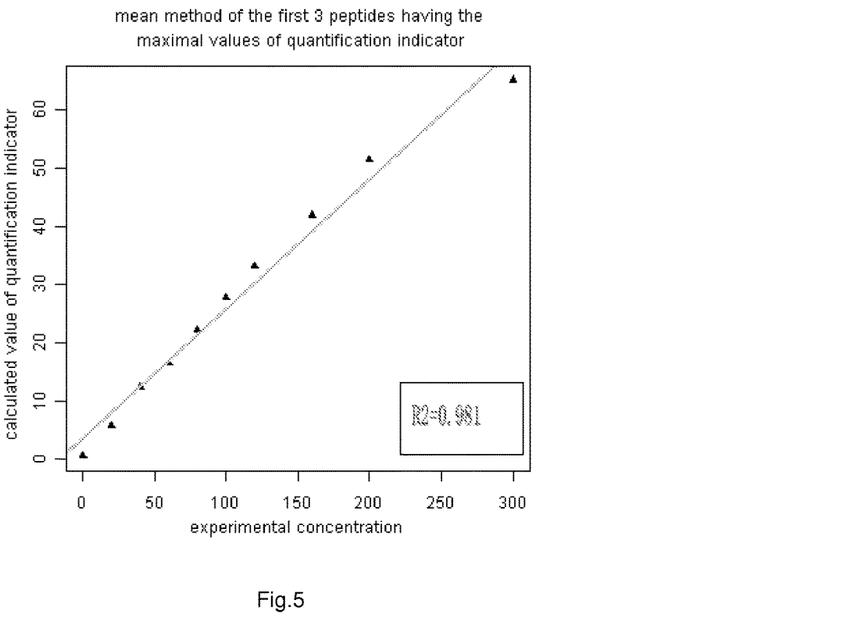
FIG. 5 is a distribution graph showing protein abundance value using a mean of first 3 peptides according to embodiments of the present disclosure.

The compared result were shown in FIG. 4 and FIG. 5, which were quantified abundance value of a standard protein and distribution of experimental concentrations obtained respectively by the method of the present disclosure and the best available method. It could be seen from the figures, linear correlation of the result obtained directly using the mean value of the first 3 peptides was 0.981, while linear correlation of the result obtained using the method of the present disclosure was 0.9933, which was obvious better than the existing best available method.

Figure 6:
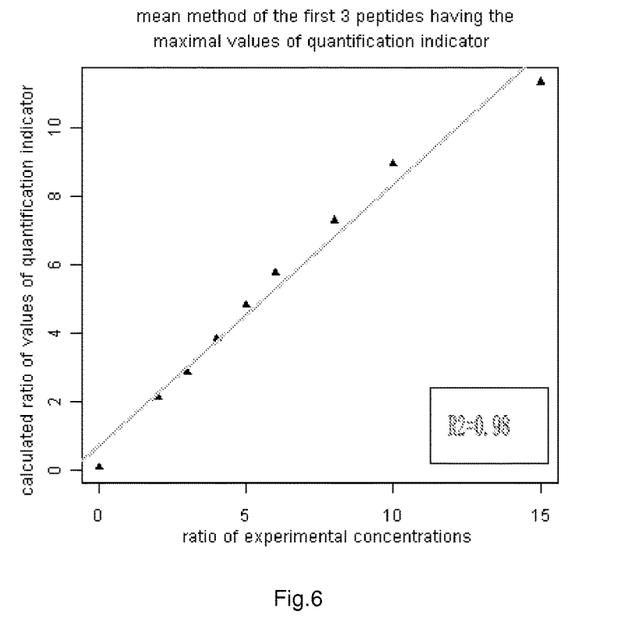
FIG. 6 is a distribution graph showing a ratio of protein abundance values using a mean value of first 3 peptides according to embodiments of the present disclosure.
Figure 7:
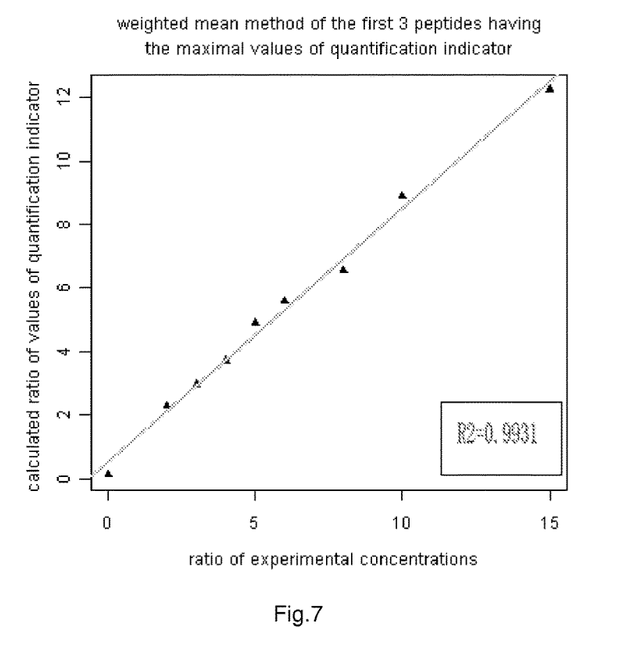
FIG. 7 is a distribution graph showing a ratio of protein abundance values using a weighted mean value of first 3 peptides according to embodiments of the present disclosure.

To illustrate the advantage of the method in the present disclosure from a level of the quantitative ratio, respective abundance values were compared ( ) with an abundance value of the other concentration of the sample, and compared with the theoretical values (0, 1, 2, 3, 4, 5, 6, 8, 10, 15). FIG. 6 was a distribution graph showing the theoretical values and the calculated values of a ratio of values of quantification indicator between different samples obtained by the existing method, while was a distribution graph showing the theoretical values and the calculated values of a ratio of values of quantification indicator between different samples obtained by the method of the present disclosure. It would be seen from FIG. 6 and FIG. 7, linear correlation between theoretical value and calculated value of a ratio of protein abundance values obtained by traditional method was 0.98, linear correlation between theoretical value and calculated value of a ratio of protein abundance values obtained by the method of the present disclosure (a weighted mean value of the first 3 peptides having the maximum values of the quantification indicator) was 0.9931. In addition, it could also been found directly from figures that the method of the present disclosure had an obvious better linear correlation comparing with that of traditional methods.

What is claimed is:

1. A method of quantifying protein abundance in a sample, comprising following steps:
    1) obtaining a plurality of primary mass spectrograms and a plurality of secondary mass spectrograms for said sample, and predicting protein fragment peptides—in a secondary mass spectrogram consulting a theoretical database;
    2) determining each protein in the sample by comparing the secondary mass spectrogram of the peptides predicted in step 1) with the theoretical database;
    3) constructing an extracted ion chromatogram (XIC) for each peptide predicted in step 1) by finding spectra peaks having a mass-to-charge value corresponding to an ion of the predicted peptides;
    4) calculating area under curve (AUC) of the XIC as a quantification indicator of the predicted peptides;
    5) for each of the proteins determined in step 2), ranking all predicted peptides by intensities and selecting those predicted peptides with top 2 intensities and top 20 intensities for calculating a weighted mean of the quantification indicators as the protein abundance in the sample.

2. The method of claim 1, further comprising a step after the step 4):
    subjecting the quantification indicators derived from all of the predicted peptides of the sample to normalization, thereby obtaining a relative quantification indicator of the predicted peptides, and
    subjecting the relative quantification indicator to step 5) instead of the quantification indicator.

3. A method of comparing a relative abundance value of a protein in samples, comprising following steps:
    1) obtaining a plurality of primary mass spectrograms and a plurality of secondary mass spectrograms for two or more of the samples, and predicting fragment peptides corresponding thereto each protein in secondary mass spectrograms;
    2) determining each protein in the sample by comparing the secondary mass spectrogram of the peptide predicted in step 1) with a reference database;
    3) constructing an extracted ion chromatogram (XIC) for each peptide predicted in step 1) by finding spectra peaks having a mass-to-charge value corresponded to an ion of the predicted peptides;
    4) calculating area under curve (AUC) of the XIC as a quantification indicator of the predicted peptides;
    5) for each of the samples, subjecting quantification indicators derived from all of the predicted peptides to normalization, thereby obtaining a relative quantification indicator of the predicted peptides;
    6) for each of the proteins determined in step 2), ranking all predicted peptides by intensities and selecting those predicted peptides with top 2 intensities and top 20 intensities for calculating a weighted mean of the relative quantification indicator as the relative abundance of the protein in the samples;
    7) calculating an abundance ratio of the protein between samples using the relative abundance of the protein, and
    8) determining whether significance of the protein abundance exists in different samples based on the abundance ratio.

4. The method of claim 1, wherein the method further comprises a step after the step 1):
    based on the predicted peptides and charges thereof, calculating a mass-to-charge value for each predicted peptide in each case of all combinations of isotopes existing in said peptide and a natural abundance value thereof; and
    ranking calculated mass-to-charge values by corresponding abundance values;
    selecting those peptides with top 2 calculated mass-to-charge values to top 20 calculated mass-to-charge values for aligning and matching to all ions in corresponding primary mass spectrogram.

5. The method of claim 3, further comprising a step prior to the step 3) of calculating the AUC of the extracted ion chromatograms:
    subjecting the extracted ion chromatograms to a filtration, comprising:
    for overlapping peaks presenting within an interval having a given retention time, removing a chromatographic peak having an AUC smaller than 50% of a total AUC of all chromatographic peaks present in the interval having the given retention time.

6. The method of claim 3, wherein trapezoid area is used for calculating the AUC of the extracted ion chromatograms in step 4).

7. The method of claim 2, further comprising a step prior to the step 5):
    in the predicted peptides corresponding to the protein, removing the quantification indicator or the relative quantification indicator which is an outlier based on Grubbs Test.

8. The method of claim 3, further comprising a step prior to the step 6):
    for each of the samples, in each of the predicted peptides corresponding to the protein, removing the relative quantification indicator which is an outlier based on Grubbs Test.

9. The method of claim 3, wherein the normalization is at least one selected from the group consisting of:
    linear regression normalization, quantile normalization, and central tendency normalization.

10. The method of claim 3, wherein the method further comprises a step after the step 1):
    based on the predicted peptides and charges thereof, calculating a mass-to-charge value for each predicted peptide in each case of all combinations of isotopes existing in said peptide and a natural abundance value thereof and ranking calculated mass-to-charge values by corresponding abundance values;

selecting those peptides with top 2 calculated mass-to-charge values to top 20 calculated mass-to-charge values for aligning and matching to all ions in corresponding primary mass spectrogram.

11. The method of claim 1, further comprising a step prior to the step 3) of calculating the AUC of the extracted ion chromatograms:

subjecting the extracted ion chromatograms to a filtration, comprising:

for overlapping peaks presenting within an interval having a given retention time, removing a chromatographic peak having an AUC smaller than 50% of a total AUC of all chromatographic peaks present in the interval having the given retention time.

12. The method of claim 1, wherein trapezoid area is used for calculating the AUC of the extracted ion chromatograms in step 4).

13. The method of claim 2, wherein the normalization is at least one selected from the group consisting of:

linear regression normalization, quantile normalization, and central tendency normalization.

\* \* \* \* \*